US012595715B2

(12) United States Patent
Amini et al.

(10) Patent No.: US 12,595,715 B2
(45) Date of Patent: Apr. 7, 2026

(54) CEMENTING LAB DATA VALIDATION BASED ON MACHINE LEARNING

(71) Applicant: Halliburton Energy Services, Inc., Houston, TX (US)

(72) Inventors: Shohreh Amini, Houston, TX (US); John Paul Bir Singh, Kingwood, TX (US); Siva Rama Krishna Jandhyala, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 1070 days.

(21) Appl. No.: 17/558,810

(22) Filed: Dec. 22, 2021

(65) Prior Publication Data

US 2023/0193720 A1     Jun. 22, 2023

(51) Int. Cl.
| | |
|---|---|
| *C04B 40/00* | (2006.01) |
| *C09K 8/46* | (2006.01) |
| *E21B 33/13* | (2006.01) |
| *E21B 47/005* | (2012.01) |
| *G06N 20/00* | (2019.01) |
| *G16C 20/30* | (2019.01) |

(52) U.S. Cl.
CPC .......... *E21B 33/13* (2013.01); *C04B 40/0032* (2013.01); *C09K 8/46* (2013.01); *E21B 47/005* (2020.05); *G06N 20/00* (2019.01); *G16C 20/30* (2019.02)

(58) Field of Classification Search
CPC ....... E21B 33/13; E21B 47/005; G06N 20/00; C04B 40/0032; G16C 20/30; C09K 8/46
See application file for complete search history.

(56) References Cited

U.S. PATENT DOCUMENTS

| | | | | |
|---|---|---|---|---|
| 6,009,419 | A | * 12/1999 | Coveney | .............. G01N 33/383 |
| | | | | 706/15 |
| 2015/0186772 | A1* | 7/2015 | Ohno | ...................... C04B 7/361 |
| | | | | 706/21 |

(Continued)

FOREIGN PATENT DOCUMENTS

| | | | |
|---|---|---|---|
| CN | 104034865 A | * | 9/2014 |
| CN | 113591374 A | | 11/2021 |

OTHER PUBLICATIONS

International Search Report and Written Opinion for PCT/2019/026175 dated Jan. 3, 2020.

(Continued)

*Primary Examiner* — Beau D Spratt

(74) *Attorney, Agent, or Firm* — Thomas Rooney; C. Tumey Law Group PLLC

(57) ABSTRACT

Techniques of the present disclosure relate to validating data for a composition design. A method comprises applying a machine learning model to at least two inputs comprising parameters of a cement composition and experimental conditions such that the machine learning model outputs at least one predicted property of the cement composition; performing a laboratory experiment to determine at least one experimental property of the cement composition; calculating an error between the at least one predicted property and the at least one experimental property; and recording the experimental data in a cement property database if the error is within an error range or repeating the performing the laboratory experiment if the error is outside the error range.

20 Claims, 5 Drawing Sheets

(56) References Cited

U.S. PATENT DOCUMENTS

2016/0092607 A1* 3/2016 Yoo .......................... G06N 3/02
                                                          706/16
2017/0364607 A1* 12/2017 Kaushik ................... C09K 8/00
2019/0105801 A1*  4/2019 Martinez ................. B28C 7/026
2020/0369942 A1* 11/2020 Singh ................. C04B 40/0032
2021/0238977 A1    8/2021 Singh et al.
2022/0107251 A1*  4/2022 Ghods ................ B28B 17/0072

OTHER PUBLICATIONS

International Search Report and Written Opinion for PCT/2019/026176 dated Jan. 3, 2020.
International Search Report and Written Opinion for PCT/2019/026179 dated Jan. 3, 2020.
U.S. Appl. No. 16/923,752 dated Jul. 8, 2020.
U.S. Appl. No. 16/923,797 dated Jul. 8, 2020.
U.S. Appl. No. 16/923,718 dated Jul. 8, 2020.
U.S. Appl. No. 17/500,116 dated Oct. 13, 2021.
International Search Report and Written Opinion for PCT/US2022/041480 dated Dec. 20, 2022.
Vakharia, V., & Gujar, R. (2019). Prediction of compressive strength and portland cement composition using cross-validation and feature ranking techniques. Construction and Building Materials, 225, 292-301.
Chaabene, W. B. et al., 'Machine learning prediction of mechanical properties of concrete: Critical review', Construction and Building Materials, 2020, vol. 260, article No. 119889, pp. 1-18 abstract; p. 15.
U.S. Appl. No. 17/546,906 dated Dec. 9, 2021.

* cited by examiner

200

206

202

204

203

TO JOB SITE

300

310

203

325

327

304

302

306

308

329

CEMENTING LAB DATA VALIDATION BASED ON MACHINE LEARNING

BACKGROUND

Cement composition designs for oil and gas wells may be performed in a lab and may include trial and error testing of cement formulations. In this process, different types of materials may be mixed to obtain desired cement properties. For each composition design, materials utilized, and subsequent test results may be recorded in a database.

Currently, the recorded data and the test results may not be screened, resulting in risks that may not be evaluated. These risks may include erroneous data entry, deviation in material performance, and questionable test results.

BRIEF DESCRIPTION OF THE DRAWINGS

These drawings illustrate certain aspects of some of the embodiments of the present method and should not be used to limit or define the method.

DETAILED DESCRIPTION

Figure 1A:
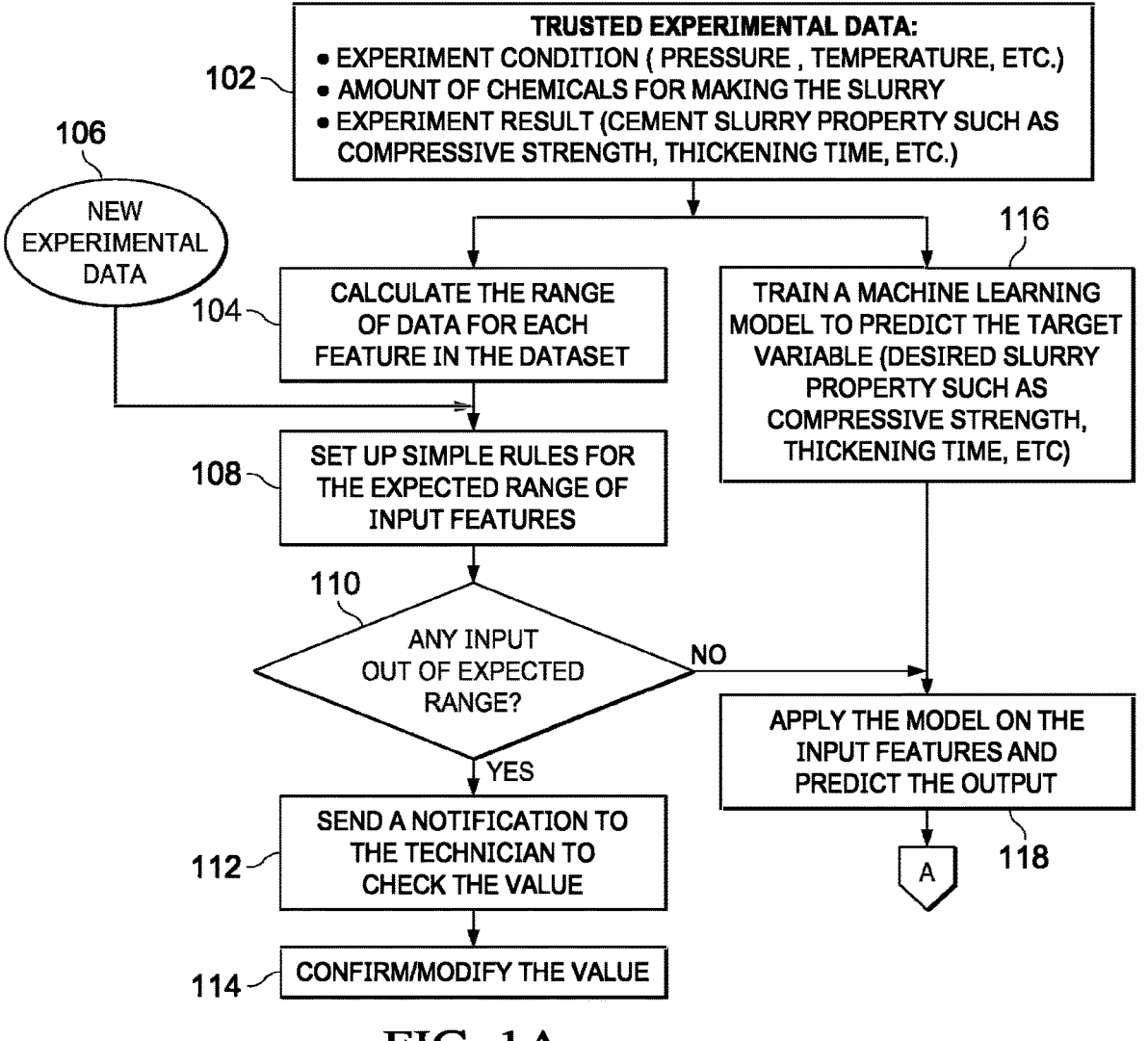
FIG. 1A illustrates a first portion of an operative flow chart for data validation, in accordance with examples of the present disclosure.

Systems and methods of the present disclosure generally relate to validation of new test data for designing a composition such as a fluid for example. The systems and methods may provide for recorded data that is valid and reliable due to an increase in accuracy of recorded test results, ensuring/maintaining consistency of components, and preventing erroneous data from being recorded in the database. The validated test data may be recorded in a database for use in making informed fluid design decisions.

In some examples, valid cement composition lab tests in the database may be utilized for new cement composition designs and production, which may decrease cost for iterative design processes for new slurries. The screening/validation workflows as described herein may be implemented with software in which the lab data is recorded.

In particular examples, a reasonable amount of reliable/trusted recorded experimental data from past experiments for the composition or components thereof may be collected. In some examples, the previously recorded data may also include a material that may include the composition or the components. Parameters of the previously recorded data may include experiment conditions (e.g., pressure, temperature), an amount of components/chemicals for making a composition, and/or experimental data (e.g., cement composition properties such as compressive strength, thickening time). The previously recorded parameters may be used to train a machine learning model which may then be used as a predictive model for any new parameters including, for example, experiment conditions (e.g., pressure, temperature), amount of components/chemicals for making the composition, and/or experiment results (e.g., cement composition properties such as compressive strength, thickening time, fluid loss, mixability, density, stability, free fluid, rheology, gel strength, permeability, Young's modulus, Poisson's ratio, cohesion, friction angle, tensile strength, shrinkage, thermal conductivity, coefficient of thermal expansion, transition time, heat of hydration. All these properties could be temperature and pressure dependent and may depend on the method of testing.

The machine learning model trained with the previously recorded data may then be used for validation of new lab tests. For example, the machine learning model may be applied to the new parameters (e.g., inputs) from the new lab tests and results may be predicted (e.g., outputs). A comparison may occur between the predicted output for the new parameters inputted into the machine learning model, and results of the new lab test. Then, any error between the new lab result (obtained in the lab and previously recorded) and the predicted result is calculated. In some examples, the workflows as described herein may be part of a quality assurance/quality control (QA/QC) test and/or a formulation test for a particular application/jobsite. The QA/QC test may be performed, for example, in the evaluation of one or more materials, such as evaluation of a cementitious component's performance.

If the error is calculated as part of a QA/QC test, an error outside of an acceptable range indicates a potential deviation in material performance. If a repeat QA/QC test confirms the error, the predictive model may flag the material in question due to its deviation from its usual performance. This allows for a decision on whether to use the batch of material in question.

If the error is calculated as part of a formulation test for a jobsite, then a notification may be generated to repeat the formulation test until the error is in an acceptable range. Then, all of the data related to the experiment (e.g., predictive model, QA/QC test, formulation tests, and/or results) may be approved and recorded in the database. Materials/fluids (e.g., cement composition design) may be produced based on this recorded data. In some examples, a notification may be generated when test results are out of a desired range.

Figure 1B:
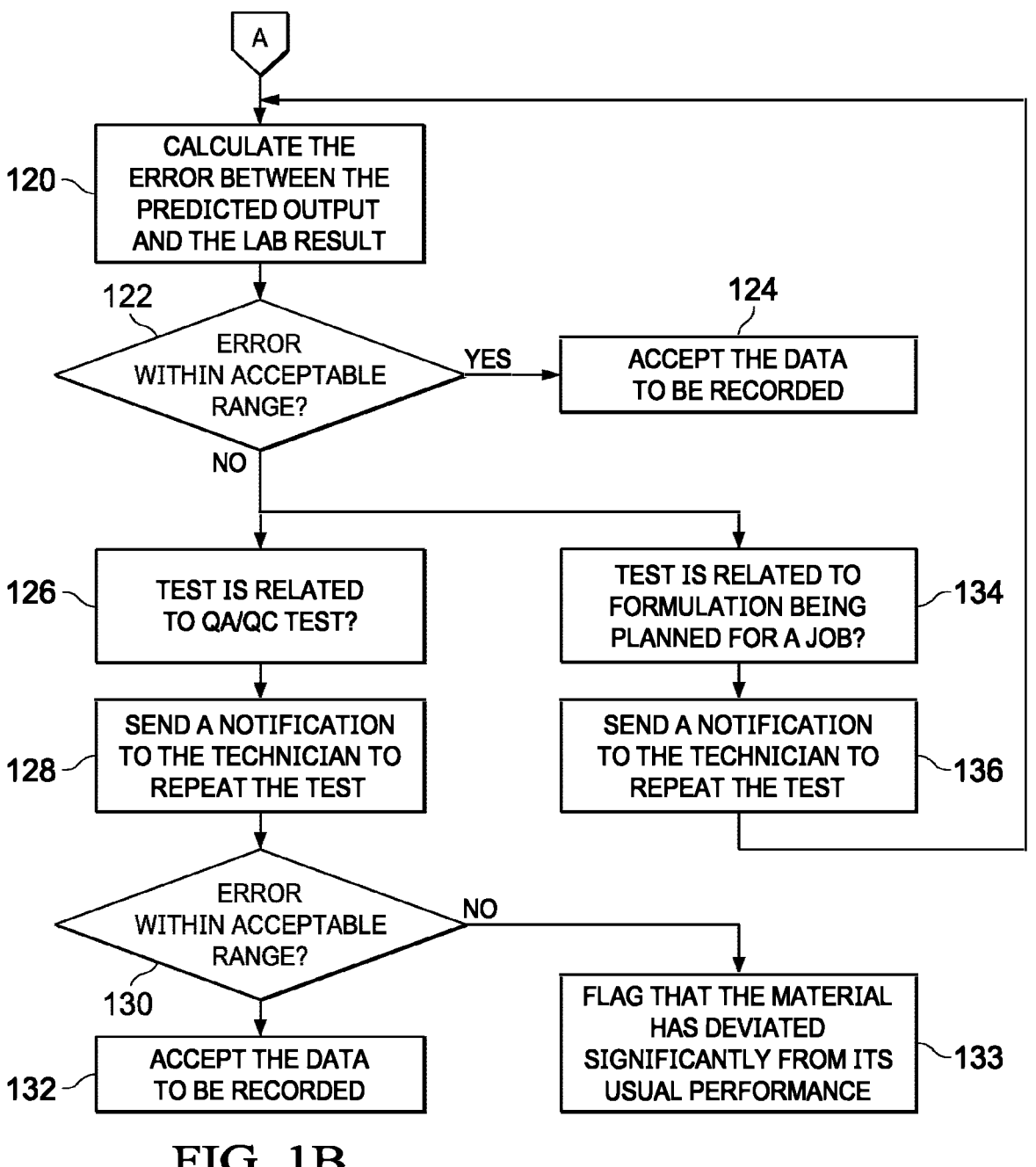
FIG. 1B illustrates a second portion of the operative flow chart for the data validation, in accordance with examples of the present disclosure.

FIGS. 1A and 1B illustrate an operative flow chart for validating new data in a database with a machine learning model, in accordance with examples of the present disclosure. With reference to FIG. 1A, at step 102, trusted previously recorded data for producing a composition(s) may include experiment conditions, amounts and identifies of components for making a composition, and/or experiment results.

The experimental data may include data for any of a variety of different experiments that can be performed for evaluation of cement composition. Each experiment can have different conditions that can impact the experimental results. experiment conditions may include any of a variety pressure and temperature, for example. The experiment conditions may include, for example, pressure, temperature which might be time dependent, pre-conditioning (also called 'conditioning') time, time for the test (such as time under temperature and pressure for curing), sample size and shape, environmental conditions such as humidity level, partial pressure of $CO_2$ and $H_2S$, etc. The experiment results may include cement composition properties such as, for example, compressive strength and thickening time. Some other cement composition properties which are tested for may include fluid loss, rheology, gel strength, mixability, free fluid, stability estimated using a settling test, transition time, permeability, shrinkage, mechanical properties including Young's modulus, Poisson's ratio, friction angle, cohesion, heat of hydration, corrosion resistance to $CO_2$ and $H_2S$ environment, amongst others. Each testing method may have its own testing protocol with multiple parameters which must be controlled and accounted for. For many of the mentioned tests, API has documented standards compiled in the API 10B-2.

The previously recorded parameters (e.g., experimental results) may be used to evaluate each new parameter or predicted output(s) for each new parameter. At step 104, a range of values for the previously recorded data (e.g., experiment conditions, experiment results, amounts of components) may be calculated. The range of values may be used, for example, as an initial screening tool when evaluating new experimental data. The range of values may be defined as the minimum value of an input variable to its max value in the data set. It may be defined as the mean +/−2*standard deviations. The factor 2 might be replaced by 3 in some cases. In other cases, the range of values may be determined by the physics or chemistry of the system. For example, it is known that maximum concentration of NaCl in water under ambient conditions is around 37%. Any value above that may not be applicable in a given system. In some other cases, the range of value may be determined by the limitations of the system such as range of temperature or pressure up to which an equipment is rated.

At step 106, new experimental data from a new lab test may be received. As will be discussed in more detail below, the machine learning model can be used for validation of this new experimental data. A laboratory test may be performed on a cement composition to obtain the experimental data. The new experimental data includes, for example, experiment conditions, experiment results, and parameters for a cement composition. This new experimental data includes new data of the type described above for the previously recorded data. In some embodiments, the new lab test is performed for evaluation of a new cement composition. For example, lab tests are performed on cement composition to determine if the cement composition has the desired properties (e.g., compressive strength, thickening time) for a particular application. The machine learning model can be used to evaluate this new experimental data and determined if the results contained in this new experimental data is accurate. In some embodiments, the lab tests may be part of a QA/QC test on a particular material in a cement composition. For example, QA/QC tests may be performed on materials (e.g., cementitious components) to evaluate whether the material performs as expected or deviates from its expected performance.

At step 108, an expected range of values for the new data may be determined/set up. At step 110, any input with a value is outside of the expected range for the new data may be determined by comparing the experimental data to the range of values. At step 112, if the input is outside of the expected range of values, a notification may be generated to check/review the input, and then at step 114, the input may be adjusted to achieve desired results.

The machine learning model may be trained to predict target values based on the known data, at step 116. In some examples, using trusted experimental data, the parameters of the machine learning model are determined during the training. The trusted data set may be divided in to three sets: training, testing, and validation sets. Training of the model may be performed by minimizing the differences between the actual experimental results and the predictions of the model using only the training set. The model may then be asked to make predictions for the data in the test set. If the predictions are not satisfactory, the model is re-trained with different set of parameters until an acceptable criterion is reached. If the predictions are acceptable, the model is then used to predict the results for the validation set. The machine learning model may be created based on any supervised learning algorithm including but not limited to Neural Network, Random Forest, and/or Decision Tree. Inputs may be inputted into the machine learning model to provide outputs. For example, a dataset may be created to include the inputs and the outputs of several lab experiments for a cement composition design. Non-limiting examples of the input features include pressure, temperature, and the amount of all the materials which are used to create the desired cement, and the output for example, may include a 24-hour compressive strength of the cement. The input dataset and the corresponding target parameter may be used to train the supervised machine learning algorithm (e.g., a neural network). The trained neural network is then able to predict the 24-hour compressive strength for a new lab experiment when the inputs and/or outputs are provided.

At step 118, if the input (experimental data) is within the expected range (at step 110), the machine learning model may be applied to the input to predict an output. For example, the experimental conditions and parameters of a cement composition (e.g., identity and concentration of components) may be input to the machine learning model. The machine learning model may then output at least one predicted property of the cement composition. Predicted properties may include any of a variety of results from laboratory experiments, such as compressive strength and thickening time. Some other cement composition properties which may be predicted include fluid loss, rheology, gel strength, mixability, free fluid, stability estimated using a settling test, transition time, permeability, shrinkage, mechanical properties including Young's modulus, Poisson's ratio, friction angle, cohesion, heat of hydration, corrosion resistance to $CO_2$ and $H_2S$ environment, amongst others With reference to FIG. 1B, at step 120, an error may be calculated between the predicted output (predicted property) for a composition and the lab result (experimental property) from the new experimental data of step 106. The lab result may be a component of the new experimental data of step 106. At step 122, if the error between the predicted output and the lab result is within an acceptable range, then the new experimental data may be accepted for recordation and subsequently recorded within the database at step 124. An acceptable error will vary depending on a number of factors, including, for example, the particular experiment performed. For example, an acceptable error for a compressive strength test may vary from an acceptable error for a thickening time test. In some embodiments, an acceptable error includes an error of less than 20%, less than 15%, less than 10%, less than 5%, or less than 1%. If recorded, the experimental data may be considered valid (or trusted) and then can be used for slurry design. For example, the cement composition used in the lab tests to obtain the new experimental data from step 106 can then be tailored and used in a subterranean treatment.

If the error is not within an acceptable range (at step 122), then at step 126, a determination of whether the experimental data is related to quality assurance/control (QA/QC) test may be made, and a notification may be generated at step 128 to repeat the QA/QC test, i.e., repeat the laboratory experiment to generate additional experimental data. In some examples, the notification may be sent, for example, to a technician. QA/QC tests may be performed, for example, to evaluate one or more materials (e.g., cementitious components) in the cement composition that was tested. The materials may be tested in a QA/QC test to determine if the materials have acceptable performance. Material performance may vary based on the particular source of the material. Thus, the QA/QC tests may be performed to evaluate whether the particular material from that source has acceptable performance.

At step 130, a determination may be made as to whether the error is within the acceptable range for the QA/QC test. The error may be determined from comparing the experimental result from the repeated laboratory experiment to the predicted property from step 118. An acceptable error will vary depending on a number of factors, including, for example, the particular experiment performed and material tested. For example, an acceptable error for a compressive strength test may vary from an acceptable error for a thickening time test. In some embodiments, an acceptable error includes an error of less than 20%, less than 15%, less than 10%, less than 5%, or less than 1%. If the error is acceptable, then at step 132, the additional experimental data from the repeated experiment may be accepted and recorded. For example, the accepted and recorded data is deemed valid for the QA/QC test, thus indicating the material test is acceptable. Acceptable material can be included in inventory for slurry development since it has acceptable performance. If the error is not acceptable, then at step 133, the machine learning model may flag the tested material as problematic for deviating from its typical performance.

Additionally, at step 122, if the error is not within an acceptable range, then at step 134, a determination whether the data is related to a formulation test for the composition for a particular jobsite may be made, and a notification may be generated at step 136 to repeat the formulation test until desired results (e.g., acceptable error) are achieved for approval and recordation for use in further experiments and/or production of desired composition(s).

Figure 2:
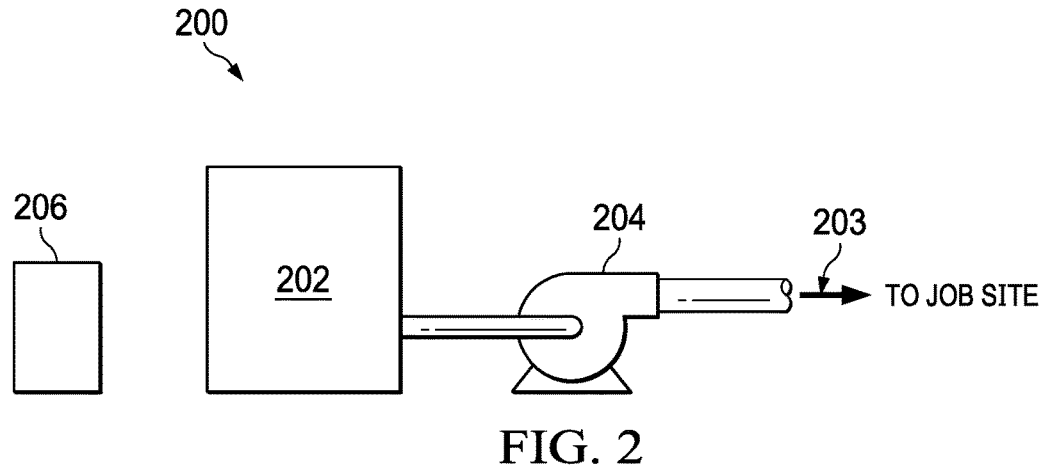
FIG. 2 illustrates a system for the preparation of a composition based on validated results, in accordance with examples of the present disclosure.

FIG. 2 illustrates a system 200 for the preparation of a composition based on validated test results, in accordance with examples of the present disclosure. As shown, components may be mixed and/or stored in a vessel 202. The vessel 202 may be configured to contain and/or mix the components to produce or modify a composition 203 (e.g., a material, a fluid, a composition, a cement). Non-limiting examples of the vessel 202 may include drums, barrels, tubs, bins, jet mixers, re-circulating mixers, and/or batch mixers. The composition 203 may then be moved (e.g., pumped via pumping equipment 204) to a location.

A computer 206 may be used for performing workflows such as shown in FIG. 1, for example. Recipes for the composition 203 may be sent to a job site for preparation by system 200. The computer 206 may be remote to the well.

The computer 206 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. The computer 206 may be any processor-driven device, such as, but not limited to, a personal computer, laptop computer, smartphone, tablet, handheld computer, dedicated process ing device, and/or an array of computing devices. In addition to having a processor, the computer 206 may include a server, a memory, input/output ("I/O") interface(s), and a network interface. The memory may be any computer-readable medium, coupled to the processor, such as RAM, ROM, and/or a removable storage device for storing data and a database management system ("DBMS") to facilitate management of data stored in memory and/or stored in separate databases.

The computer 206 may also include display devices such as a monitor featuring an operating system, media browser, and the ability to run one or more software applications. Additionally, the computer 206 may include non-transitory computer-readable media. Non-transitory computer-readable media may include any instrumentality or aggregation of instrumentalities that may retain data and/or instructions for a period of time.

Figure 3:
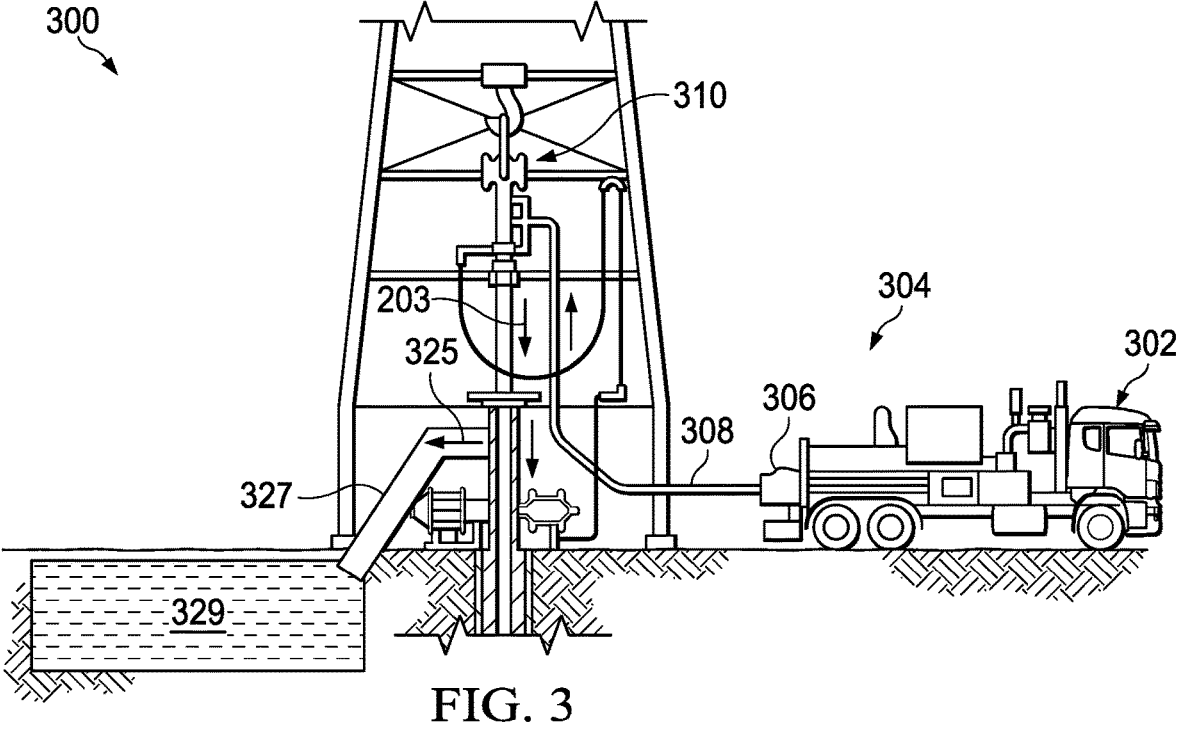
FIG. 3 illustrates a system that may be used for the placement of the validated composition, in accordance with examples of the present disclosure.

FIG. 3 illustrates a system 300 that may be used in the placement of the composition that is prepared based on validated test results, in accordance with examples of the present disclosure. It should be noted that while FIG. 3 generally depicts a land-based operation, those skilled in the art will readily recognize that the principles described herein are equally applicable to subsea operations that employ floating or sea-based platforms and rigs, without departing from the scope of the disclosure.

The system 300 may include a cementing unit 302, which may include one or more cement trucks, for example. The cementing unit 302 may include mixing equipment 304 and pumping equipment 306. The cementing unit 302 may pump the composition 203, through a feed pipe 308 and to a cementing head 310 which conveys the composition 203 into a downhole environment.

Figure 4:
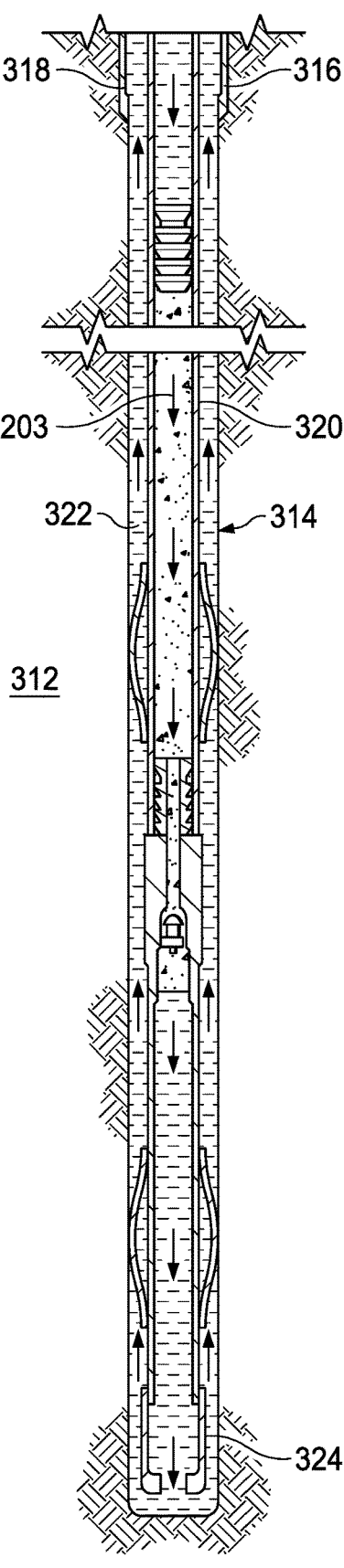
FIG. 4 illustrates the validated composition disposed within a subterranean formation, in accordance with particular examples of the present disclosure.

With additional reference to FIG. 4, the composition 203 may be placed in a subterranean formation 312. A wellbore 314 may be drilled into the subterranean formation 312. While the wellbore 314 is shown generally extending vertically into the subterranean formation 312, the principles described herein are also applicable to wellbores that extend at an angle through subterranean formation 312, such as horizontal and slanted wellbores.

A first section 316 of casing may be inserted into the wellbore 314. The section 316 may be cemented in place by a cement sheath 318. A second section 320 of casing may also be disposed in the wellbore 314. A wellbore annulus 322 formed between the second section 320 and walls of the wellbore 314 and/or the first section 316.

The composition 203 may be pumped down the interior of the second section 320 of casing. The composition 203 may be allowed to flow down the interior of the casing through the casing shoe 324 at the bottom of the second section 320 and up around the second section 320 of casing into the wellbore annulus 322. As it is introduced, the composition 203 may displace other fluids 325, such as drilling fluids and/or spacer fluids that may be present in the interior of the casing and/or the wellbore annulus 322. At least a portion of the displaced fluids 325 may exit the wellbore annulus 322 via a flow line 327 and be deposited, for example, in one or more retention pits 329.

Other techniques may also be utilized for introduction of the composition 203. For example, reverse circulation techniques may be used that include introducing the composition 203 into the subterranean formation 312 via the wellbore annulus 322 instead of through the casing (e.g., section 320).

Figure 5:
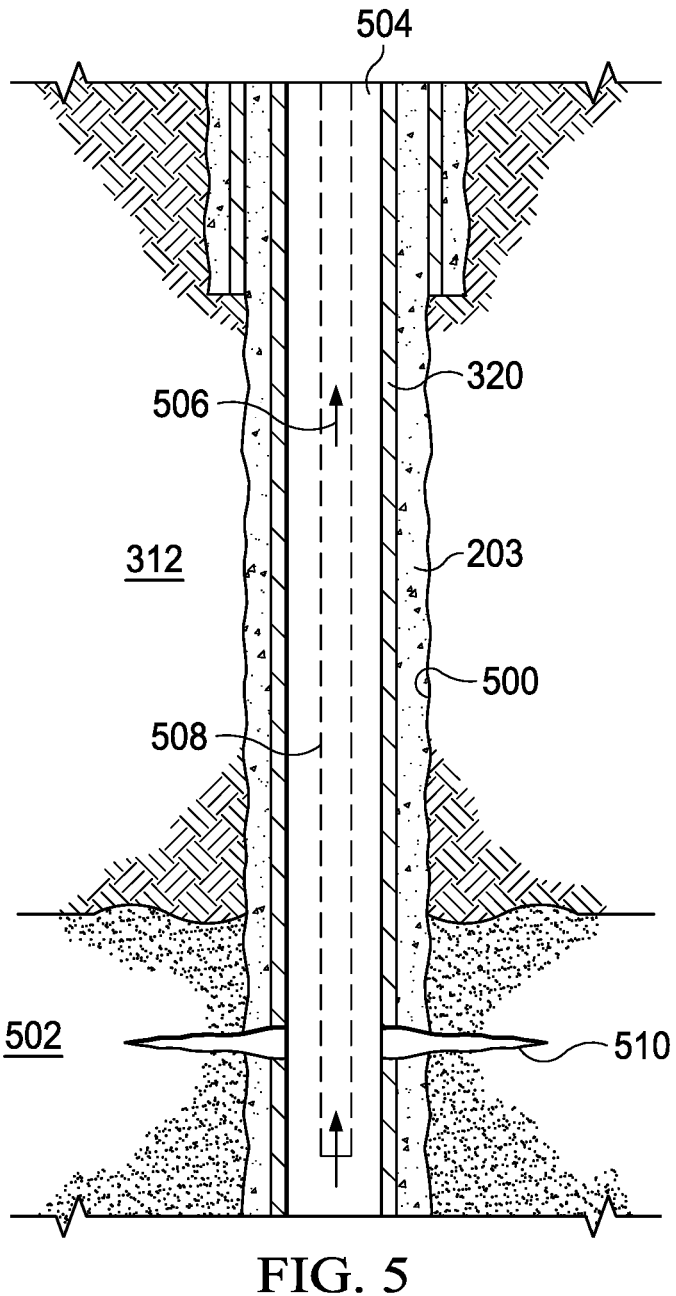
FIG. 5 illustrates the validated composition set within the subterranean formation, in accordance with particular examples of the present disclosure.

With additional reference to FIG. 5, the composition 203 may then be allowed to set in the wellbore annulus 322, for example, to form a second cement sheath 500 that supports and positions the second section 320 of casing in the wellbore 314.

Hydrocarbons may then flow from a producing zone 502 of the subterranean formation 312 up through the second section 320 of casing and to a surface 504, as illustrated by arrows 506. Production tubing 508 may be disposed in the second section 320 of casing to produce the hydrocarbons. In some examples, perforations 510 may extend into the subterranean formation 312.

Accordingly, the present disclosure may relate to techniques for validating data that may be used for composition designs for wellbore operations. The systems and methods may include any of the various features disclosed herein, including one or more of the following statements.

Statement 1. A method comprises applying a machine learning model to at least two inputs comprising parameters of a cement composition and experimental conditions such that the machine learning model outputs at least one predicted property of the cement composition, wherein the two or more inputs comprise parameters of the cement composition and experimental conditions; performing a laboratory experiment to determine at least one experimental property of the cement composition; calculating an error between the at least one predicted property and the at least one experimental property; and recording the experimental data in a cement property database if the error is within an error range or repeating the performing the laboratory experiment if the error is outside the error range.

Statement 2. The method of the statement 1, further comprising training the machine learning model to predict properties of cement compositions.

Statement 3. The method of any of the preceding statements, sending a notification to the user about deviation in material performance if the error is outside the error range.

Statement 4. The method of any of the preceding statements, further comprising determining a range of values for the two or more inputs to screen the inputs prior to an application of the machine learning model to the inputs.

Statement 5. The method of any of the preceding statements, wherein the parameters of the cement composition each individually comprise at least one parameter selected from the group consisting of an experimental condition, an amount of a component of the cement composition, an identify of a component of the cement composition, and combinations thereof.

Statement 6. The method of any of the preceding statements, wherein the at least one predicted property comprises at least one cement property selected from the group consisting of compressive strength, thickening time, fluid loss, and combinations thereof.

Statement 7. The method of any of the preceding statements, further comprising training the machine learning model with previous recorded cement data.

Statement 8. The method of any of the preceding statements, further comprising screening the at least two inputs with a predetermined range.

Statement 9. The method of any of the preceding statements, further comprising producing an additional cement composition based on the cement composition, wherein the error is within the error range.

Statement 10. The method of any of the preceding statements, further comprising pumping the additional cement composition in a wellbore.

Statement 11. calculating an acceptable range of values for properties of cement compositions based on previously recorded experimental data; receiving new experimental data for a cement composition, wherein the experimental data comprises at least one experimental property of the cement composition; comparing the at least one experimental property to determine if the experimental data is within the acceptable range of values; applying a machine learning model to at least two inputs comprising parameters of a cement composition and experimental conditions such that the machine learning model outputs at least one predicted property of the cement composition; calculating an error between at least one predicted property and the at least one experimental property; recording the experimental data in a cement property database, wherein the error is within an error range; and producing an additional cement composition based on the cement composition.

Statement 12. The method of any of the statement 11, further comprising training the machine learning model with previously recorded cement data, prior to application of the machine learning model to the inputs.

Statement 13. The method of the statement 11 or the statement 12, further comprising training the machine learning model with previously recorded data.

Statement 14. The method of any of the statements 11-13, further comprising sending a notification to a user about deviation in material performance if the error is outside the error range.

Statement 15. The method of any of the statements 11-14, further comprising disposing the additional cement composition into a wellbore.

Statement 16. A method comprising: training a machine learning model to predict properties of cement compositions based on previously recorded experimental data; calculating an acceptable range of values for one or more properties in the experimental data; performing a laboratory experiment to determine at least one experimental property of a cement composition; applying the machine learning model to at least two inputs comprising parameters of a cement composition and experimental conditions such that the machine learning model outputs at least one predicted property of the cement composition; calculating an error between the at least one predicted property and the at least one experimental property, wherein the at least one experimental property is within the acceptable range of values; and recording the experimental data in a cement property database if the error is within a range or repeating the performing the laboratory experiment if the error is outside the error range.

Statement 17. The method of any of the statement 16, further comprising producing an additional cement composition based on the cement composition, wherein the error is within the error range, and disposing the cement composition into a wellbore.

Statement 18. The method of any of the statements 16 or 17, wherein the parameters of the cement composition each individually comprise at least one parameter selected from the group consisting of an experimental condition, an amount of a component of the cement composition, an identify of a component of the cement composition, and combinations thereof.

Statement 19. The method of any of the statements 16-18, wherein the at least one predicted property comprises at least one cement property selected from the group consisting of compressive strength, thickening time, fluid loss, and combinations thereof.

Statement 20. The method of any of the statements 16-19, further comprising sending a notification to a user about deviation in material performance if the error is outside the error range.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

For the sake of brevity, only certain ranges are explicitly disclosed herein. However, ranges from any lower limit may be combined with any upper limit to recite a range not explicitly recited as well as ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, as the present embodiments may be modified and practiced in different but equivalent manners. Although individual embodiments are discussed, all combinations of each embodiment are contemplated and covered by the disclosure. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
applying a machine learning model trained on previously recorded experimental data comprising parameters of a plurality of historical cement composition and historical experimental condition, to at least two inputs comprising parameters of a cement composition comprising a cement and water and experimental conditions such that the machine learning model outputs at least one predicted property of the cement composition, wherein properties of a cement composition comprise at least one of compressive strength, thickening time, or gel strength and wherein experimental conditions comprise at least of pressure, temperature, or time;
performing a laboratory experiment to determine at least one experimental property of the cement composition;
calculating an error between the at least one predicted property and the at least one experimental property;

10 recording the experimental data in a cement property database if the error is within an error range or repeating the performing the laboratory experiment if the error is outside the error range; and
preparing an additional cement composition based on the cement composition, such that at least one of the parameters of the additional cement composition has a second error within the error range.

2. The method of claim 1, further comprising training the machine learning model to predict properties of cement compositions.

3. The method of claim 1, further comprising sending a notification to a user about deviation in material performance if the error is outside the error range.

4. The method of claim 1, further comprising determining a range of values for the two or more inputs to screen the inputs prior to an application of the machine learning model to the inputs.

5. The method of claim 1, wherein the parameters of the cement composition each individually comprise at least one parameter selected from the group consisting of an experimental condition, an amount of a component of the cement composition, an identify of a component of the cement composition, and combinations thereof.

6. The method of claim 1, wherein the at least one predicted property comprises at least one cement property selected from the group consisting of compressive strength, thickening time, fluid loss, and combinations thereof.

7. The method of claim 1, further comprising training the machine learning model with previous recorded cement data.

8. The method of claim 1, further comprising screening the at least two inputs with a predetermined range.

9. The method of claim 1, further comprising pumping the additional cement composition in a wellbore.

10. The method of claim 1 wherein the laboratory experiment comprises a QA/QC test, wherein the QA/QC test determines the performance of cement composition materials and/or wherein the laboratory experiment comprises a formulation test, wherein the formulation test determines cement composition properties.

11. The method of claim 1 further comprising allowing the additional cement composition to set to form a set composition.

12. A method comprising:
calculating an acceptable range of values for properties of cement compositions based on previously recorded experimental data;
receiving new experimental data for a cement composition, wherein the experimental data comprises at least one experimental property of the cement composition comparing the at least one experimental property to determine if the experimental data is within the acceptable range of values;
applying a machine learning model to at least two inputs comprising parameters of a cement composition comprising a cement and water and experimental conditions such that the machine learning model outputs at least one predicted property of the cement composition, wherein properties of a cement composition comprise at least one of compressive strength, thickening time, or gel strength and wherein experimental conditions comprise at least of pressure, temperature, or time;
calculating an error between at least one predicted property and the at least one experimental property;
recording the experimental data in a cement property database, wherein-if the error is within an error range or repeating receiving new experimental data from a repeated laboratory experiment if the error is outside the error range; and producing an additional cement composition based on the cement composition, such that at least one of the parameters of the additional cement composition has a second error within the error range.

13. The method of claim 12, further comprising training the machine learning model with previously recorded cement data, prior to application of the machine learning model to the inputs.

14. The method of claim 12, further comprising training the machine learning model with previously recorded data.

15. The method of claim 12, further comprising sending a notification to a user about deviation in material performance if the error is outside the error range.

16. The method of claim 12, further comprising disposing the additional cement composition into a wellbore.

17. A method comprising:

training a machine learning model to predict properties of cement compositions based on previously recorded experimental data;

calculating an acceptable range of values for one or more properties in the experimental data;

performing a laboratory experiment to determine at least one experimental property of a cement composition;

applying the machine learning model to at least two inputs comprising parameters of a cement composition comprising a cement and water and experimental conditions such that the machine learning model outputs at least one predicted property of the cement composition, wherein properties of a cement composition comprise at least one of compressive strength, thickening time, or gel strength and wherein experimental conditions comprise at least of pressure, temperature, or time;

calculating an error between the at least one predicted property and the at least one experimental property, wherein the at least one experimental property is within the acceptable range of values;

recording the experimental data in a cement property database if the error is within a range or repeating the performing the laboratory experiment if the error is outside the error range; and preparing an additional cement composition based on the cement composition, such that at least one of the parameters of the additional cement composition has a second error within the error range.

18. The method of claim 17, wherein the parameters of the cement composition each individually comprise at least one parameter selected from the group consisting of an experimental condition, an amount of a component of the cement composition, an identify of a component of the cement composition, and combinations thereof.

19. The method of claim 17, wherein the at least one predicted property comprises at least one cement property selected from the group consisting of compressive strength, thickening time, fluid loss, and combinations thereof.

20. The method of claim 17, further comprising sending a notification to a user about deviation in material performance if the error is outside the error range.

* * * * *